(12) United States Patent
Zheng et al.

(10) Patent No.: US 9,242,965 B2
(45) Date of Patent: Jan. 26, 2016

(54) PROCESS FOR THE MANUFACTURE OF (E)-4-N,N-DIALKYLAMINO CROTONIC ACID IN HX SALT FORM AND USE THEREOF FOR SYNTHESIS OF EGFR TYROSINE KINASE INHIBITORS

(71) Applicant: Boehringer Ingelheim International GmbH, Ingelheim am Rhein (DE)

(72) Inventors: Juncheng Zheng, Shanghai (CN); Da Deng, Shanghai (CN); Guanghua Lv, Shanghai (CN); Jun Yan, Shanghai (CN); Joerg Brandenburg, Wiesbaden (DE); Jutta Kroeber, Bingen (DE); Ulrich Scholz, Bad Kreuznach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/576,849

(22) Filed: Dec. 19, 2014

(65) Prior Publication Data

US 2015/0183764 A1    Jul. 2, 2015

(30) Foreign Application Priority Data

Dec. 31, 2013 (WO) ............... PCT/CN2013/091071

(51) Int. Cl.

| | | |
|---|---|---|
| C07C 227/00 | (2006.01) |
| C07D 405/00 | (2006.01) |
| C07C 221/00 | (2006.01) |
| C07D 405/04 | (2006.01) |
| C07C 227/18 | (2006.01) |
| C07C 227/16 | (2006.01) |
| C07C 227/10 | (2006.01) |

(52) U.S. Cl.
CPC ............ *C07D 405/04* (2013.01); *C07C 221/00* (2013.01); *C07C 227/10* (2013.01); *C07C 227/16* (2013.01); *C07C 227/18* (2013.01)

(58) Field of Classification Search
CPC .. C07C 227/10; C07C 227/16; C07C 227/18; C07C 221/00; C07C 223/10; C07C 229/30; C07D 405/04
USPC ............................. 562/574; 564/296; 544/283
See application file for complete search history.

(56) References Cited

U.S. PATENT DOCUMENTS

| | | | |
|---|---|---|---|
| 4,933,443 A | 6/1990 | Hamashima et al. |
| 5,728,687 A | 3/1998 | Bissery |
| 5,866,572 A | 2/1999 | Barker et al. |
| 6,127,374 A | 10/2000 | Bridges |
| 6,153,617 A | 11/2000 | Bridges |
| 6,217,866 B1 | 4/2001 | Schlessinger et al. |
| 6,251,912 B1 | 6/2001 | Wissner et al. |
| 6,297,258 B1 | 10/2001 | Wissner et al. |
| 6,344,459 B1 | 2/2002 | Bridges et al. |
| 6,362,336 B1 | 3/2002 | Lohmann et al. |
| 6,403,580 B1 | 6/2002 | Himmelsbach et al. |
| 6,617,329 B2 | 9/2003 | Himmelsbach et al. |
| 6,627,634 B2 | 9/2003 | Himmelsbach et al. |
| 6,653,305 B2 | 11/2003 | Himmelsbach et al. |
| 6,656,946 B2 | 12/2003 | Himmelsbach et al. |
| 6,673,803 B2 | 1/2004 | Thomas et al. |
| 6,740,651 B2 | 5/2004 | Himmelsbach et al. |
| 6,924,285 B2 | 8/2005 | Himmelsbach et al. |
| 6,972,288 B1 | 12/2005 | Himmelsbach et al. |
| 7,019,012 B2 | 3/2006 | Himmelsbach et al. |
| 7,084,136 B2 | 8/2006 | Tanimoto et al. |
| 7,119,084 B2 | 10/2006 | Himmelsbach et al. |
| 7,160,889 B2 | 1/2007 | Hennequin et al. |
| 7,196,091 B2 | 3/2007 | Himmelsbach et al. |
| 7,220,750 B2 | 5/2007 | Himmelsbach et al. |
| 7,223,749 B2 | 5/2007 | Himmelsbach et al. |
| 7,456,189 B2 | 11/2008 | Himmelsbach et al. |
| 7,846,936 B2 | 12/2010 | Hilberg et al. |

(Continued)

FOREIGN PATENT DOCUMENTS

| | | |
|---|---|---|
| CN | 103755688 A | 4/2014 |
| DE | 19825591 A1 | 12/1999 |

(Continued)

OTHER PUBLICATIONS van Erp et al.; Clinical pharmacokinetics of tyrosine kinase inhibitors; Cancer Treatment Reviews; vol. 35; No. 8; Dec. 1, 2009; pp. 692-706.

Vlahovic, G., et al., "Activation of Tyrosine Kinases in Cancer", The Oncologist, 2003, vol. 8, pp. 531-538.

Wikstrand, C. et al. "Monoclonal Antibodies against EGFRvIII Are Tumor Specific and React with Breast and Lung Carcinomas and Malignant Gliomas." Cancer Research, 1995, vol. 55, No. 14, pp. 3140-3148.

(Continued)

*Primary Examiner* — Sikarl Witherspoon
(74) *Attorney, Agent, or Firm* — Michael P. Morris; Alan R. Stempel

(57) ABSTRACT

The present invention is directed to an efficient process for the manufacture of (E)-4-N,N-dialkylamino crotonic acid in HX salt form of formula I

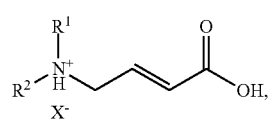

wherein $R^1$ and $R^2$ independently denote $C_{1-3}$-alkyl groups and $X^-$ denotes an acid anion, such as the chloride, bromide, tosylate, mesylate or trifluoroacetate anion, with high quality, and a process for synthesis of EGFR tyrosine kinase inhibitors with heterocyclic quinazoline, quinoline or pyrimidopyrimidine core structure, using the acid addition salt I and activated derivatives thereof as intermediates.

6 Claims, No Drawings

(56) References Cited

U.S. PATENT DOCUMENTS

| | | |
|---|---|---|
| 7,960,546 B2 | 6/2011 | Schroeder et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 8,404,697 B2 | 3/2013 | Solca et al. |
| 2001/0044435 A1 | 11/2001 | Himmelsbach et al. |
| 2002/0032208 A1 | 3/2002 | Lohmann et al. |
| 2002/0077330 A1 | 6/2002 | Himmelsbach et al. |
| 2002/0082270 A1 | 6/2002 | Himmelsbach et al. |
| 2002/0169180 A1 | 11/2002 | Himmelsbach et al. |
| 2002/0173509 A1 | 11/2002 | Himmelsbach et al. |
| 2003/0149062 A1 | 8/2003 | Jung et al. |
| 2003/0186956 A1 | 10/2003 | Bilke et al. |
| 2003/0191308 A1 | 10/2003 | Hennequin et al. |
| 2003/0225079 A1 | 12/2003 | Singer et al. |
| 2004/0024019 A1 | 2/2004 | Tanimoto et al. |
| 2004/0057992 A1 | 3/2004 | Gierer |
| 2004/0158065 A1 | 8/2004 | Barth et al. |
| 2005/0031769 A1 | 2/2005 | Watanabe et al. |
| 2005/0043233 A1 | 2/2005 | Stefanic et al. |
| 2005/0085495 A1 | 4/2005 | Soyka et al. |
| 2005/0215574 A1 | 9/2005 | Bradbury et al. |
| 2006/0058311 A1 | 3/2006 | Munzert et al. |
| 2006/0100223 A1 | 5/2006 | Himmelsbach et al. |
| 2006/0270672 A1 | 11/2006 | Himmelsbach et al. |
| 2007/0009533 A1 | 1/2007 | Sikic et al. |
| 2007/0027170 A1 | 2/2007 | Soyka et al. |
| 2007/0078091 A1 | 4/2007 | Hubler et al. |
| 2007/0099918 A1 | 5/2007 | Singer et al. |
| 2007/0185091 A1 | 8/2007 | Himmelsbach et al. |
| 2008/0096212 A1 | 4/2008 | Bell et al. |
| 2008/0103161 A1 | 5/2008 | Himmelsbach et al. |
| 2008/0145422 A1 | 6/2008 | Zhou et al. |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0269487 A1 | 10/2008 | Bradbury et al. |
| 2009/0036676 A1 | 2/2009 | Himmelsbach et al. |
| 2009/0203683 A1 | 8/2009 | Himmelsbach et al. |
| 2009/0238828 A1 | 9/2009 | Munzert et al. |
| 2009/0306044 A1 | 12/2009 | Solca et al. |
| 2009/0306072 A1 | 12/2009 | Jung et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0087482 A1 | 4/2010 | Haber et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0136826 A1 | 6/2011 | Hilberg et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0046494 A1 | 2/2012 | Choi et al. |
| 2012/0107399 A1 | 5/2012 | Barta |
| 2012/0157472 A1 | 6/2012 | Larsen et al. |
| 2012/0294867 A1 | 11/2012 | Denis et al. |
| 2012/0329778 A1 | 12/2012 | Himmelsbach et al. |
| 2013/0012465 A1 | 1/2013 | Haslinger et al. |

FOREIGN PATENT DOCUMENTS

| | | |
|---|---|---|
| DE | 19908567 A1 | 8/2000 |
| DE | 19911366 A1 | 9/2000 |
| DE | 10017539 A1 | 10/2001 |
| DE | 10042060 A1 | 3/2002 |
| DE | 10042064 A1 | 3/2002 |
| EP | 0302967 A2 | 2/1989 |
| EP | 0566226 A1 | 10/1993 |
| EP | 0799619 A2 | 10/1997 |
| EP | 1123705 A1 | 8/2001 |
| EP | 2612860 A1 | 7/2013 |
| WO | 9410995 A1 | 5/1994 |
| WO | 9520045 A1 | 7/1995 |
| WO | 9630347 A1 | 10/1996 |
| WO | 9633980 A1 | 10/1996 |
| WO | 9702266 A1 | 1/1997 |
| WO | 9738983 A1 | 10/1997 |
| WO | 9843960 A1 | 10/1998 |
| WO | 9906378 A1 | 2/1999 |
| WO | 9906396 A1 | 2/1999 |
| WO | 9909016 A1 | 2/1999 |
| WO | 9935146 A1 | 7/1999 |
| WO | 9965228 A2 | 12/1999 |
| WO | 0018740 A1 | 4/2000 |
| WO | 0031048 A1 | 6/2000 |
| WO | 0031068 A1 | 6/2000 |
| WO | 0051991 A1 | 9/2000 |
| WO | 0055141 A1 | 9/2000 |
| WO | 0078735 A1 | 12/2000 |
| WO | 0134574 A1 | 5/2001 |
| WO | 0168186 A2 | 9/2001 |
| WO | 0177104 A1 | 10/2001 |
| WO | 0218351 A1 | 3/2002 |
| WO | 0218372 A1 | 3/2002 |
| WO | 0218373 A1 | 3/2002 |
| WO | 0218375 A1 | 3/2002 |
| WO | 0218376 A1 | 3/2002 |
| WO | 0241882 A2 | 5/2002 |
| WO | 0250043 A1 | 6/2002 |
| WO | 03082290 A1 | 10/2003 |
| WO | 03089439 A1 | 10/2003 |
| WO | 03094921 A2 | 11/2003 |
| WO | 2004014426 A1 | 2/2004 |
| WO | 2004066919 A2 | 8/2004 |
| WO | 2004074263 A1 | 9/2004 |
| WO | 2004096224 A2 | 11/2004 |
| WO | 2004108664 A2 | 12/2004 |
| WO | 2005023315 A2 | 3/2005 |
| WO | 2005028470 A1 | 3/2005 |
| WO | 2005033096 A1 | 4/2005 |
| WO | 2005037824 A2 | 4/2005 |
| WO | 2005094357 A2 | 10/2005 |
| WO | 2006017317 A2 | 2/2006 |
| WO | 2006018182 A1 | 2/2006 |
| WO | 2006084058 A2 | 8/2006 |
| WO | 2006127207 A1 | 11/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2008091701 A2 | 7/2008 |
| WO | 2009030239 A1 | 3/2009 |
| WO | 2009147238 A1 | 12/2009 |
| WO | 2010048477 A2 | 4/2010 |
| WO | 2010081817 A1 | 7/2010 |
| WO | 2010085845 A1 | 8/2010 |
| WO | 2010129053 A2 | 11/2010 |
| WO | 2011003853 A2 | 1/2011 |
| WO | 2011056894 A2 | 5/2011 |
| WO | 2011069962 A1 | 6/2011 |
| WO | 2012156437 A1 | 11/2012 |
| WO | 2013173254 A1 | 11/2013 |

OTHER PUBLICATIONS

Wissner, A. et al., "Synthesis and Structure—Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)." Journal of Medicinal Chemistry, 2003, vol. 46, pp. 49-63.

Xu, Y. et al., "Acquired Resistance of Lung Adenocarcinoma to EGFR-tyrosine Kinase Inhibitors Gefitinib and Erlotinib." Cancer Biology & Therapy, 2010, vol. 9, No. 8, pp. 572-582.

Yanase, K. et al., "Gefitinib reverses breast cancer resistance protein-medicated drug resistance". Molecular Cancer Therapeutics, 2004, Vo. 9, No. 9, p. 1119-1125.

(56) References Cited

OTHER PUBLICATIONS

Yanase, K. et al., "Gefitinib reverses breast cancer resistance protein-medicated drug resistance". Molecular Cancer Therapeutics, 2004, Vo. 9, No. 9, p. 119-1125.

Yang, J. C-H, et al., "Afatinib for patients with lung adenocarcinoma and epidermal growth factor receptor mutations (LUX-Lung 2): a phase 2 trial", The Lancet, Oncology, vol. 13, May 2012, pp. 539-548.

Yoshimura, N. et al., "EKB-569, a new irreversible epidermal growth factor recptor tyrosine kinase inhibitor, with clinical activity in patients with non-small cell lung cancer with acquired resistance to gefitinib." Lung Cancer, 2006, vol. 51, pp. 363-368.

Zhou, W. et al., "Novel mutant-selective EGFR kinase inhibitors against EGFR T790M." Nature, 2009, vol. 462, pp. 1070-1074.

Kawabata, S. et al., "Abstract 2417: A new mouse model for epithelial ear neoplasms based upon expression of mutant EGFRL858R/T790M." Cancer Research, 2011, vol. 71, No. 8, p. 1.

Kobayashi, S. et al., "EGFR Mutation and Resistance of Non-Small-Cell Lung Cancer to Gefitinib." The New England Journal of Medicine, 2005, vol. 352, pp. 786-792.

Krozely, P. Abstract—Clinical Journal of Oncology Nursing, 2004, vol. 8, No. 2, p. 1092-1095.

Kwak, E. et al. "Irreversible Inhibitors of the EGF Receptor may Circumvent Acquired Resistance to Gefitinib." PNAS, 2005, vol. 102, No. 21, pp. 7665-7670.

Kwak, E.L. et al., "Irreversible inhibitors of the EGF receptor may circumvent acquired resistance of gefitinib." Proceedings of National Academy of Sciences of the USA, 2005, vol. 102, No. 21, pp. 7665-7670.

Laack et al.; Lessons learnt from gefitinib and erlotinib: Key insights into small-molecule EGFR-targeted kinase inhibitors in non-small cell lung cancer; Lung Cancer; vol. 69; No. 3; Sep. 1, 2010; pp. 359-264.

Laird & Cherrington, "Small molecule tyrosine kinase inhibitors: clinical development of anticancer agents" Expert Opinion. Investig. Drugs.; Ashley Publications (2003) 12(1) p. 51-64.

Lee, M., "Tamsulosin for the Treatment of Benigh Prostatic Hypertrophy". The Annals of Pharmacotherapy, Feb. 2000, 34, p. 188-199.

Lewis, N., et al. Abstract: "A phase I dose escalation study of BIBW 2992, an irreversible dual EGFR/HER2 receptor tyrosine kinase inhibitor, in a 3 week on 1 week off schedule in patients with advanced solid tumors". Journal of Clinical Oncology, 2006 ASCO Annual Meeting Proceedings (Post-Meeting Edition). vol. 24, No. 18S (Jun. 20 Supplement), 2006: 3091.

Li, D. et al. "BIBW2992, An Irreversible EGFR/HER2 Inhibitor Highly Effective in Preclinical Lung Cancer Models." Oncogene, 2008, vol. 27, No. 34, pp. 4702-4711.

Lin; Drug-drug interaction mediated by inhibition and induction of P-glycoprotein; Advanced Drug Delivery Reviews; vol. 55; No. 1; Jan. 21, 2003; pp. 53-81.

Martins, R.G. et al., "Cisplatin and Radiotherapy With or Without Erlotinib in Locally Advanced Squamous Cell Carcinoma of the Head and Neck: A Randomized Phase II Trial." Journal of Clinical Oncology, 2013, vol. 31, No. 11, pp. 1415-1421.

McMahon; VEGF Receptor Signaling in Tumor Angiogenesis; The Oncologist; 2000; 5 (suppl 1); pp. 3-10.

Medina et al.; Lapatinib: A Dual Inhibitor of Human Epidermal Growth Factor Receptor Tyrosine Kinases; Clinical Therapeutics; vol. 30; No. 8; Aug. 2008; pp. 1426-1447.

Miller, V.A., et al., "Afatinib versus placebo for patients with advanced, metastatic non-small-cell lung cancer after failure of erlotinib, gefitinib, or both, and one or two lines of chemotherapy (LUX-Lung1): a phase 2b/3 randomised trial", The Lancet, Oncology, vol. 19, May 2012, pp. 528-538.

Mills; Humidity Control in Pharma Processing; Innovations in Pharmaceutical Technology; 2007; pp. 1-3.

Minkovsky et al.; BIBW-2992, a dual receptor tyrosine kinase inhibitor for the treatment of solid turmors; Current Opinion in Investigational Drugs, Pharmapress; vol. 9; No. 12; Dec. 1, 2008; pp. 1336-1346.

National Cancer Institute, Cancer Drug Information, Cetuximab. Posted: Oct. 5, 2006, Updated: Dec. 30, 2010.

Nosov et al., "Mekhanismy regulyatsii vnutrikletochnoi peredachi signala . . . " VIII Rossiskii Onkologicheskii Congress—Moscow, 2004.

Paez, J. G. "EGFR Mutations in Lung Cancer: Correlation with Clinical Response to Gefitinib Therapy". Science, vol. 304, 2004, p. 1497-1500.

Pinedo et al.; Translational Research: The Role of VEGF in Tumor Angiogenesis; The Oncologist; 2000; 5(suppl 1); pp. 1-2.

Plummer et al.; 573 Poster Phase I study of BIBW2992, an oral irreversible dual EGFR/HER2 inhibitor, showing activity in tumors with mutated EGFR; European Journal of Cancer; Supplement; Nov. 2006; vol. 4; No. 12; Pergamon; Oxford, GB.

Prescribing Information, Package insert for Erbitux, Revised Jul. 2009, pp. 1-24.

Ramalingam, S. et al., "Dual Inhibition of the Epidermal Growth Factor Receptor with Cetuximab, an IgG1 Monoclonal Antibody, and Gefitinib, A Tyrosine Kinase Inhibitor, in Patients with Refractory Non-small Cell Lung Cancer (NSCLC): A Phase I Study." Journal of Thoracic Oncology, 2008, vol. 3, No. 3, pp. 258-264.

Rayford, W. et al., "Muscarinic Cholinergic Receptors Promote Growth of Human Prostate Cancer Cells". The Prostate, Feb. 1997, 30(3), p. 160-165.

Regales, L. et al., "Dual targeting of EGFR can overcome a major drug resistance mutation in mouse models of EGFR mutant lung cancer", American Society for Clinical Investigation, vol. 199, No. 10, Oct. 1, 2009, p. 3000-3010.

Reid, A, et al, "Dual inhibition of ErbB1 (EGFR/HER1) and ErbB2 (HER2/neu)", European Journal of Cancer, Pergamon Press, Oxford, GB, vol. 43, No. 3, Feb. 1, 2008, p. 481-489.

Rosell, R. et al., "Crossing the Rubicon in Lung Adenocarcinoma: the Conundrum of EGFR Tyrosine Kinase Mutations." 2005, vol. 1, No. 3, pp. 319-322.

Sausville, E. A. et al. "Contributions of Human Tumor Xenografts to Anticancer Drug Development". Cancer Research, 2006, vol. 66 (7), p. 3351-3354.

Seimbille, Y. et al., "Fluorine-18 labeling of 6,7-disubstituted anilinoquinazoline deratives for poistron emission tomography (PET) imaging of tyrosine kinase receptors: synthesis of 18F-Iressa and related molecular probes." Journal of Labelled Compounds and Radiopharmaceuticals, 2005, vol. 48, No. 11, pp. 829-843.

Seiwert, T.Y. et al., "A randomized, phase II study of afatinib versus cetuximab in metastatic or recurrent squamous cell carcinoma of the head and neck." Annals of Oncology, 2014, vol. 25, No. 9, pp. 1813-1820.

Sequist, L.V. et al., "1229PD / Lux-Lung 3: Symptom and Health-Related Quality of Life Results from a Randomized Phase III Study in 1st-Line Advanced NSCLC Patients Harbouring EGFR Mutations", Poster Discussion, Sep. 30, 2012 [downloaded from the internet Oct. 25, 2012. http://abstracts.webges.com/myitinerary/session-148.html?congress=esmo2012#.UFdGtBr1LSY.gmai].

Sequist, L.V. et al., "Neratinib, an Irreversible Pan-ErbB Receptor Tyrosine Kinase Inhibitor: Results of a Phase II Trial in Patients With Advanced Non-Small-Cell Lung Cancer." Journal of Clinical Oncology, 2010, vol. 28, No. 18, pp. 3076-3083.

Sequist, L.V., et al., "Neratinib, an Irrerversible Pan-ErbB Receptor Tyrosine Kinase Inhibitor: Results of a Phase II Trial in Patients with Advanced Non-Small-Cell Lung Cancer" Journal of Clinical Oncology, vol. 28, No. 18, Jun. 20, 2010, p. 3076-3083.

Shi, Zhi et al., "Inhibiting the function of ABCB1 and ABCG2 by the EGFR tyrosine kinase inhibitor AG1478." Biochemical Pharmacology, 2009, vol. 77, pp. 781-793.

Slobbe, P. et al., "PET imaging with small-molecule tyrosine kinase inhibitors: TKI-PET." Drug Discovery Today, 2012, vol. 17, No. 21-22, pp. 1175-1187.

Solca et al., Abstracts of AACR-EORTC International Conference, Molecular Targets and Cancer Therapeutics.

(56) References Cited

OTHER PUBLICATIONS

Solca et al.; 567 Poster Efficacy of BIBW 2992, an irreversible dual EGFR/HER2 receptor tyrosine kinase inhibitor, in combination with cytotoxic agents; European Journal of Cancer; Supplement; Nov. 2006; vol. 4; No. 12; Pergamon; Oxford, GB.
Solca, F. et al., "A242 BIBW 2992, an Irreversible Dual EGFR/HER2 Kinase Inhibitor, Shows Activity on L858R/T790M EGFR Mutants." and "A244 BIBW 2992, An Irreversible Dual EGFR/HER2 Receptor Tyrosine Kinase Inhibitor for Cancer Therapy." Molecular Targets and Cancer Therapeutics, Nov. 2005.
Stedman's Medical Dictionary, 27th edition, Lippincott, Williams & Wilkins, Baltimore, 2000.
Stopfer, P. et al., "Afatinib pharmacokinetics and metabolism after oral administration to healthy male volunteers." Cancer Chemotherapy and Pharmacology, 2012, vol. 69, No. 4, pp. 1051-1061.
Subramaniam, D. S., et al., "BIBW 2992 in non-small cell lung cancer". Expert Opinion, Drug Evaluation, 2011, vol. 20, No. 3, p. 415-422.
Subramaniam, D.S. et al., "BIBW 2992 in non-small cell lung cancer". Expert Opinion Investig. Drugs, 2011, 20(3), p. 415-422.
Supplement ASCO Meeting Abstracts 1-4, Journal of Clinical Oncology, 2006.
Swaisland et al.; Pharmacokinetic Drug Interactions of Gefitinib with Rifampicin, Itraconazole and Metoprolol; Clinical Pharmacokinetics; vol. 44; No. 10; Jan. 1, 2005; pp. 1067-1081.
The Lancet, "Cetuximab in NSCLC: another trial needed." www.thelancet.com/oncology,. vol. 12, Jan. 2011.
Toyooka, S. et al., "EGFR Mutation and Response of Lung Cancer to Gefitinib." The New England Journal of Medicine, 2005, vol. 352, No. 20, p. 2136.
Tsou, Hwei-Ru, "6-Substituted-4-(3-bromophenylamino)quinazolines as Putative Irreversible Inhibitors of the Epidermal Growth Factor Receptor (EGFR) and Human Epidermal Growth Facotr Receptor (HER-2) Tyrosine Kinases with Enhanced Antitumore Activity", J. Med. Chem 2001, 2719-2734, vol. 44.
U.S. Appl. No. 12/914,003, filed Oct. 28, 2010, Inventor: Frank Himmelsbach.
"Afatinib Prolongs Progression—Free Survival in NSCLC", 2012 ASCO Annual Meeting, Chicago, ASCO Daily News, LBA7500, Jun. 1-5, 2012. [downloaded from the internet Oct. 25, 2012. http://chicago2012.asco.org/ASCODailyNews/LBA7500.aspx].
Abstract in English (2000) for DE19911366.
Abstract in English for CN 103755688, publication date Apr. 30, 2014.
Abstract in English for WO199965228, 2010.
Agarwal et al.; Distribution of Gefitinib to the Brain Is Limited by P-glycoprotein (ABCB1) and Breast Cancer Resistance Protein (ABCG2)-Mediated Active Efflux; Journal of Pharmacology and Experimental Therapeutics; vol. 334; No. 1; Jul. 2010; pp. 147-155.
Agus, D.B. et al., Abstract: "A phase I dose escalation study of BIBW 2992, an irreversible dual EGFR/HER2 receptor tyrosine kinase inhibitor, in a continuous schedule in patients with advanced solid tumours." Journal of Clinical Oncology, 2006, ASCO Annual Meeting Proceedings (Post-Meeting Edition). vol. 24, No. 18S, (Jun. 20 Supplement), 2006, 2074.
Alan, R. "Benign Prostatic Hyperplasia (BPH)". Available at http://healthlibrary.epnet.com/GetContent/asp?token-1baaea3c-d4f5-4e14-8429-e3b3e1add7a7&chunkiid-1203, last reviewed Mar. 2006.
Argiris, A. et al., "Phase III Randomized, Placebo-Controlled Trial of Docetaxel With or Without Gefitinib in Recurrent or Metastatic Head and Neck Cancer: An Eastern Cooperative Oncology Group Trial." Journal of Clinical Oncology, 2013, vol. 31, No. 11, pp. 1405-1414.
Barton, J. et al., "Growth Factors and their Receptors: new Targets for Prostate Cancern Therapy". Urology 58 (Supplement 2A), Aug. 2001, p. 114-122.
Bell, D.W. et al., "Inherited susceptibility to lung cancer may be associated with the T790M drug resistance mutation in EGFR". Nature Genetics, Dec. 2005, vol. 37, No. 12, p. 1315-1316. Published online Oct. 30, 2005.

Boehringer Ingelheim Press Release "Resistance to Epidermal Growth Factor Receptor (EGFR) Tyrosine Kinase Inhibitors (TKIs)." 2010.
Boehringer Ingelheim, "BIBW 2992: A Potent and Irreversible Inhibitor of EGFR/HER1 and HER2." Accessed on Jan. 3, 2012.
Boschelli, D., "4-Anilino-3-quinolinecarbonitriles: An Emerging Class of Kinase Inhibitors—An Update." Medicinal Chemistry Reviews—Online, 2004, vol. 1, pp. 457-463.
Burris, Ha et al.; "EGF1004: a randomized, multicenter, phase Ib study of the safety, biologic activity and clinical efficacy of the dual kinase inhibitor GW572016" Breast Cancer Research and Treatment, V. 82, suppl. 1 (2003), p. S18 #39.
Calabrisi, P. et al., Goodman * Gilman. "Section IX Chemotherapy of Neoplastic Diseases—Introduction". Goodman & Gilman's The Pharmacological Basis of Therapeutics, 10th ed, 2001, Hardman, JG, Limbird LE, Gilman AG, Eds. McGraw-Hill, NY, 2001, p. 1381-1388 (pp. 1381m 1383-1385 and 1388 provided).
Camp, E. et al., "Molecular Mechanisms of Resistance to Therapies Targeting the Epidermal Growth Factor Receptor." Clinical Cancer Research, 2005, vol. 11, No. 1, pp. 397-405.
Cancer Genome and Collaborative Group. Nature, Brief Communications Sep. 2004, vol. 431, p. 525-526.
Cancer Genome and Collaborative Group. Nature, Brief Communications, Sep. 2004, vol. 431, p. 525-526.
Carter, T.A. et al., "Inhibition of drug-resistant mutants of ABL, KIT, and EGF receptor kinases." Proceedings of National Academy of Sciences of the USA, 2005, vol. 102, No. 31, pp. 11011-11016.
Cascone, T. et al, "Epidermal growth factor receptor inhibitors in non-small-cell lung cancer", Expert Opinion on Drug Discovery, Informa Healthcare, London, GB, vol. 2, No. 3, Mar. 1, 2008, p. 335-348.
Cetuximab—FDA Approval, Department of Health and Human Services Letter to ImClone Systems, Inc., dated Feb. 12, 2004.
Cetuximab-EMEA. Erbitux, EPAR (European Public Assessment Report) Summary for the Public, Doc. Ref.: EMEA/327144/2009. EMEA/H/C/558. Jun. 2009.
Cetuximab-Erbitux Label, 2004.
Chan, S.K. et al., "Mutations of the epidermal growth factor receptor in non-small cell lung cancer—Search and destroy." European Journal of Cancer 42, 2006, pp. 17-23.
Chen et al.; Epidermal Growth Factor Receptor Inhibitors: Current Status and Future Directions; Current Problems in Cancer; Mosby, St. Louis, MO; vol. 33; No. 4; Jul. 1, 2009; pp. 245-294.
Chhun et al.; Gefitinib-phenytoin interaction is not correlated with the 14C-erythromycin breath test in healthy male volunteers; British Journal of Clinical Pharmacology; vol. 68; No. 2; Aug. 2009; pp. 226-237.
Choong, N. et al., "Gefitinib Response of Erlotinib-refractory Lung Cancer Involving Meninges—Role of EGFR Mutation." Nature Clinical Practice Oncology, 2006, vol. 3, No. 1, pp. 50-57.
Chustecka, Zosia, "Afatinib Shows Modest Benefit in Head and Neck Cancer." Boehringer Ingelheim, European Society for Medical Oncology (ESMO) Congress 2014, Presented Sep. 27, 2014, Medscape.com.
Collins et al.; Tyrosine kinase inhibitors potentiate the cytotoxicity of MDR-substrate anticancer agents independent of growth factor receptor status in lung cancer cell lines; Invest New Drugs; vol. 28; No. 4; Jun. 5, 2009; pp. 433-444.
deMiguel, M. et al., "Immunohistochemical comparative analysis of transforming grwoth factor a, epidermal growth factor, and epidermal growth factor receptor in normal, hyperplastic and neoplastic human prostates". Cytokine, 1998, p. 722-727.
Di Leo, A. et al., "Phase III, Double-Blind, Randomized Study Comparing Lapatinib Plus Paclitaxel With Placebo Plus Paclitaxel as First-Line Treatment for Metastatic Breast Cancer." Journal of Clinical Oncology, 2007, vol. 26, No. 34, pp. 5544-5552.
Doebele, R. et al., "New strategies to overcome limitations of reversible EGFR tyrosine kinase inhibitor therapy in non-small cell lung cancer." Lung Cancer, 2010, vol. 69, pp. 1-12.
Drug Data Report, "BIBW-2992" 2005, vol. 27, No. 11.

(56) References Cited

OTHER PUBLICATIONS

Duque, J.L. et al., "Heparin-Binding Epidermal Growth Factor-Like Growth Factor is an Autocrine Mediator of Human Prostate Stromal Cell Growth in Vitro". The Journal of Urology, vol. 165, Jan. 2001, p. 284-288.
European Society for Medical Oncology, "ESMO 2014 Press Release: Second-Line Afatinib Significantly Improves Progression-Free Survival in Recurrent or Metastatic Head and Neck Cancer, Phase III Trial Shows." Retrieved online Dec. 18, 2014. http://www.esmo.org/Conferences/ESMO-2014-Congress/Press-Media/Second-Line-Afatinib-Significantly-Improves-Progression-Free-Survival-in-Recurrent-or-Metastatic-Head-and-Neck-Cancer-Phase-III-Trial-Shows.
European Society for Medical Oncology, "ESMO 2014: Afatinib vs Methotrexate in Second-Line Treatment of Recurrent and/or Metastatic Head and Neck Squamos Cell Carcinoma." Retrieved online Dec. 18, 2014. http://www.esmo.org/Conferences/ESMO-2014-Congress/News-Articles/Afatinib-vs-Methotrexate-in-Second-Line-Treatment-of-Recurrent-and-or-Metastatic-Head-and-Neck-Squamous-Cell-Carcinoma.
Fry, David W., "Inhibition of the Epidermal Growth Factor Receptor Family of Tyrosine Kinases as an Approach to Cancer Chemotherapy Progression from Reversible to Irreversible Inhibitors." Pharmacological & Therapeutics, 1999, vol. 82, No. 2-3, pp. 207-218.
Gelovani, Juri G., "Molecular imaging of epidermal growth factor receptor expression-activity at the kinase level in tumors with positron emission tomography." Cancer and Metastasis Reviews, 2008, vol. 27, No. 4, pp. 645-653.
Gonzales-Barcena, D. et al., "Responses to the antagonistic analog of LH-RH (SB-75, cetrorelix) in patients with benign prostatic hyperplasia and prostatic cancer". The Prostate, 1994, 24(2), p. 84-92, only abstract provided.
Goodman & Gilman's, "The Pharmacological Basis of Therapeutics" Tenth Edition, 2001, pp. 1381-1388.
Hansen, A.R. et al., "Epidermal Growth Factor Receptor Targeting in Head and Neck Cancer: Have We Been Just Skimming the Surface?" Journal of Clinical Oncology, 2013, vol. 31, No. 11, pp. 1381-1383.
Harari, P.M. "Epidermal growth factor receptor inhibition strategies in oncology". Endocrine-Related Cancer, 2004, vol. 11. p. 689-708.
Herbst, R.S. et al., "Monoclonal Antibodies to Target Epidermal Growth Factor Receptor-Positive Tumors". Cancer, Mar. 1, 2002, vol. 94, No. 5, p. 1593-1611.
Hirsh, V., "Afatinib (BIBW 2992) development in non-small-cell lung cancer". Future Oncol., 2011, 7(7), p. 817-825.
Hirsh, V., "Afatinib (BIBW 2992) Development in Non-Small-Cell Lung Cancer." Future Oncology, 2011, vol. 7, pp. 817-825.
Hofmann, B. B., Chapter 10 Catecholamines, Sympathomimetic Drugs, and Adrenergic Receptor Antagonists. "Goodman and Gilman's The Pharmacological Basis of Therapeutics, 10th ed." Hardman JG, Limbird, LE, and Gilman AG, Eds. McGraw-Hill, 2001, p. 215-268, pp. 215, 247 and 248 provided).
Humblet, Y. "Cetuximab: An IgG1 monoclonal antibody for the treatment of epidermal growth factor receptor-expressing tumours". Expert Opinion. Drug Evaluation. Ashley Publications, 2004, p. 1621-1633.
International Search Report and Written Opinion for PCT/EP2014/079150 mailed Mar. 23, 2015.
Janjigian, Y. et al., "Phase I/II Trial of Cetuximab and Erlotinib in Patients with Lung Adenocarcinoma and Acquired Resistance to Erlotinib." Clinical Cancer Research, 2011, vol. 17, No. 8, pp. 2521-2527.
Johnson, J, et al. "Relationships between drug activity in NCI preclinical in vitro and in vitro and in vivo models and early clinical trials". British Journal of Cancer, 2001, 84 (10, p. 1424-1431.

PROCESS FOR THE MANUFACTURE OF (E)-4-N,N-DIALKYLAMINO CROTONIC ACID IN HX SALT FORM AND USE THEREOF FOR SYNTHESIS OF EGFR TYROSINE KINASE INHIBITORS

BACKGROUND OF THE INVENTION

1. Technical Field

The present invention is directed to an efficient process for the manufacture of (E)-4-N,N-dialkylamino crotonic acid in HX salt form of formula I

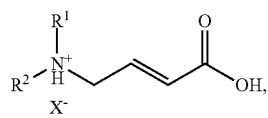

wherein $R^1$ and $R^2$ independently denote $C_{1-3}$-alkyl groups and $X^-$ denotes an acid anion, such as the chloride, bromide, tosylate, mesylate or trifluoroacetate anion, with high quality, and a process for synthesis of EGFR tyrosine kinase inhibitors with heterocyclic quinazoline, quinoline or pyrimidopyrimidine core structure, using an acid addition salt I and activated derivatives thereof as intermediates.

2. Background Information

Epidermal growth factor receptor (EGFR) tyrosine kinase inhibitors have been studied clinically to demonstrate efficacy in treating certain cancers. Compounds which inhibit signal transduction by tyrosine kinases, for example of the human EGF receptor, have been shown to be useful for treating pathophysiological processes caused by hyperfunction of tyrosine kinases. David W. Fry, *Pharmacol. Ther. Vol.* 82, Nos. 2-3, pp. 207-218, 1999. Several irreversible inhibitors have been shown to have therapeutic advantages such as prolonged tumor suppression compared to reversible inhibitors such as gefitinib. DeBono & Rowinsky, *Br. Med. Bull.* 64:227-254 (2002).

The compounds of formula I and the salts thereof are suitable as a valuable intermediates in the synthesis of EGFR tyrosine kinase inhibitors based on a quinazoline, quinoline or pyrimidopyrimidine core structure. Examples of such EGFR tyrosinekinase inhibitors are HKI-272 (INN: Neratinib, in phase III clinical development for treatment of breast cancer), BIBW 2992 (INN: Afatinib, approved in the US and Europe for the treatment of non-small cell lung cancer patients with tumors bearing EGFR mutations), EKB-569 (INN: Pelitinib) or HKI 357.

BIBW 2992 is disclosed specifically in WO 02/50043. This compound is a highly selective, potent, irreversible dual inhibitor of erbb1 receptor (EGFR) and erbB2 (Her2/neu) receptor tyrosine kinases, suitable for the treatment of e.g. benign or malignant tumours, particularly tumours of epithelial and neuroepithelial origin, metastasis and the abnormal proliferation of vascular endothelial cells (neoangiogenesis), for treating diseases of the airways and lungs which are accompanied by increased or altered production of mucus caused by stimulation by tyrosine kinases, as well as for treating diseases of the gastrointestinal tract and bile duct and gall bladder which are associated with disrupted activity of the tyrosine kinases. Promising effects in treatment of non-small cell lung cancer (NSCLC) patients have been reported already in Drugs of the Future 2008, 33(8): 649-654; and by Li, D. et al, in *Oncogene* (2008) 27, 4702-4711.

Pharmaceutical formulations of the compound are disclosed in the documents cited hereinbefore and in WO 2009/147238, indications to be treated and combination treatments are disclosed in WO 2007/054550 and WO 2007/054551. Skin toxicity and diarrhea are the most common adverse events in patients with adenocarcinoma of the lung and activating EGFR mutations, treated with this class of compounds (Mukherji, D., et al, *Expert Opin. Investig. Drugs* (2009) 18(3), 293-300).

Methods for the preparation of BIBW 2992 are described in WO 02/50043, WO 2005/037824 and WO 2007/085638.

WO 2002/50043 discloses a method of production in which aminocrotonylamino-substituted quinazolines are prepared in a one-pot reaction from the corresponding aniline component, bromocrotonic acid, oxalyl chloride and a secondary amine (Scheme 1).

Scheme 1:

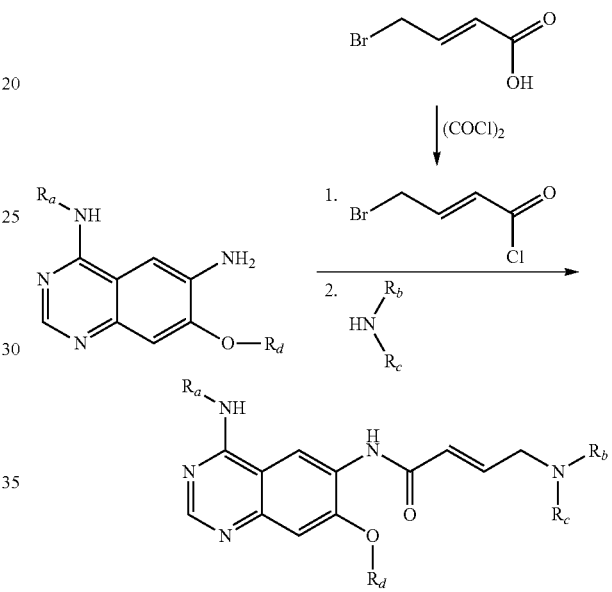

The process is not well suited to technical use on an industrial scale, as the yields obtained are at most 50% and as a rule laborious purification by column chromatography is needed. Moreover the educt bromocrotonic acid is not commercially available in large amounts and the corresponding methyl bromocrotonate is only available with a purity of about 80%.

WO 2005/037824 discloses a method of preparation wherein BIBW 2992 is prepared using a Wittig-Horner-Emmons like process wherein the corresponding aminoquinazoline is reacted with diethylphosphonoacetic acid after activation to form a quinazoline substituted in 6-position by a carbamoyl-diethylphosphonate group, which is reacted in a second step with 2-dialkylaminoacetaldehyde or a corresponding aldehyde equivalent such as a corresponding acetale to form the unsaturated side chain in position 6 (Scheme 2).

Scheme 2:

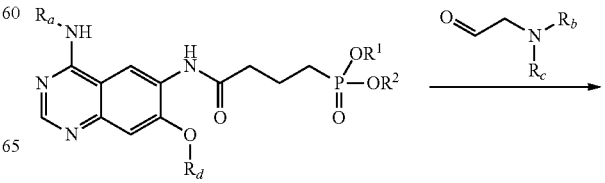

-continued

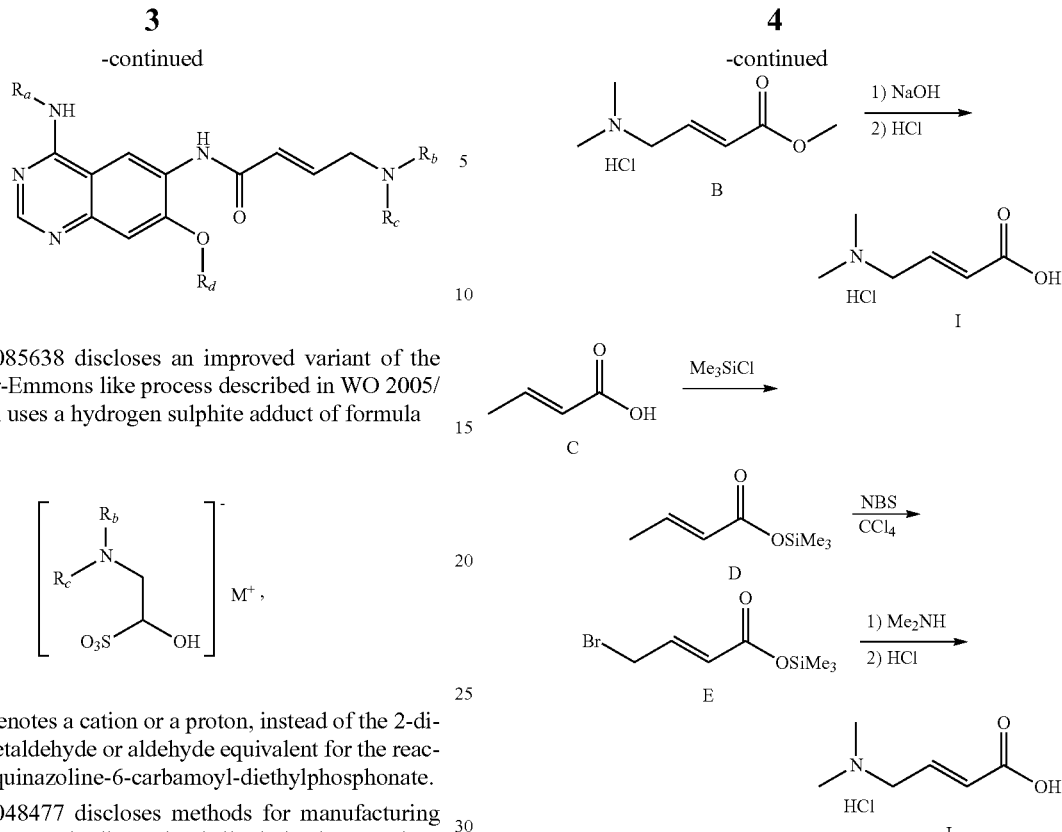

WO 2007/085638 discloses an improved variant of the Wittig-Horner-Emmons like process described in WO 2005/037824 which uses a hydrogen sulphite adduct of formula wherein $M^+$ denotes a cation or a proton, instead of the 2-dialkylaminoacetaldehyde or aldehyde equivalent for the reaction with the quinazoline-6-carbamoyl-diethylphosphonate.

WO 2010/048477 discloses methods for manufacturing certain 4-amino-3-quinolinecarbonitrile derivatives, such as HKI-272, using stabilized 4-(amino)-2-butenoyl chloride intermediates (for example, 4-(dimethylamino)-2-butenoyl chloride) for coupling a 4-(amino)-2-butenoyl group to an amino group (—$NH_2$) at the 6- or 7-position of a 4-amino-3-quinolinecarbonitrile. WO 2004/066919 and WO 2006/127207 both disclose preparation of 4-(dialkylamino)-2-butenoyl chloride by reaction of N,N-dialkylamino crotonic acid hydrochloride with oxalylchloride and subsequent amid coupling of 4-(dialkylamino)-2-butenoyl chloride with 4-amino-3-quinolinecarbonitrile.

Different routes to compound I or salts thereof are known in the art, but they all suffer from severe drawbacks from a commercial manufacturing point of view. They also do not allow for the control of the quality of the product in a way that is requested for the production of pharmaceutical intermediates. Therefore it was necessary to develop a novel route to compound I circumventing these problems.

As a very important intermediate in drug synthesis, different synthetic routes were developed to manufacture compound I. Most commonly the substitution between a dialkylamine with (E)-4-bromocrotonate was utilized as the key synthesis strategy.

In WO 2004/066919 two routes are documented employing brominated compounds A and E as key intermediates, as shown in Scheme 3.

Scheme 3 Synthesis of compound I according to WO 2004/066919

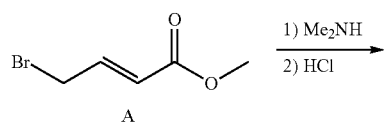

Regarding the route starting with compound A, only about 30% total yield was achieved for overall two steps, and the purity of obtained compound I was insufficient (92%) for pharmaceutical production purpose. This is mainly due to the reasons, first, that purity of commerically available compound A is only very moderate, and, second, that hydrolysis occuring under basic conditions easily leads to by-products. Both drawbacks render final purification very difficult and cause low efficiency.

In the alternative route starting with compound C, some severe problems need to be solved before scale-up. These problems are, first, the use of highly toxic solvent $CCl_4$, and, second, the silane reagent which may block the waste gas combustion system by the formation of sand.

WO 2010/131921 (corresponding to US 2012046494 A1) discloses an improved process for preparation of compound I providing better quality compared to the process according to WO 2004/066919. This improvement could be achieved by using compound H in high quality and performing hydrolysis of compound J under acidic conditions (Scheme 4). However, this process suffers from several issues with regard to scale up such as, first, the use of bromine which should be avoided in production scale, second, the use of large amounts of environment-unfriendly solvent dichloromethane, third, extensive work required to obtain pure compound H which needs vacuum distillation, and, fourth, tedious work to distill off great amounts of water during the hydrolysis step, e.g. about 7 ml of water to obtain 1 g of compound H.

All those issues together with the linear synthetic strategy (total yield was around 38%) lead to high expenditure regarding Volume-Time-Output and consequently less competitive.

Scheme 4 Synthesis of compound I according to WO2010/131921.

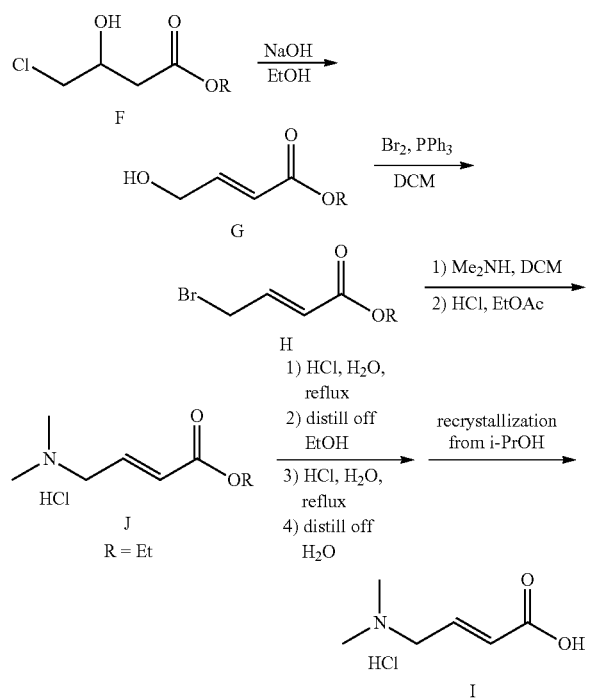

In the light of the above disadvantages of the known methods of production there was a strong need for a novel or improved process to manufacture the compounds of formula I and the salts thereof. Thus the aim of the present invention is to provide a process which allows the synthesis of the desired product on commercial scale with high quality and in a competitive manner, using highly pure starting materials which are readily available and without any high technical expenditure. Preferably the process according to the invention should be environment friendly and sustainable, avoiding toxic reactants or solvents as well as complex, expensive or time-consuming purification processes and energy consuming reaction steps. As a matter of course, the process of the invention should provide the compounds of formula I and the salts thereof in a quality suitable for use in production of pharmaceuticals according to GMP standards, especially for use in production of EGFR tyrosine kinase inhibitors based on a quinazoline, quinoline or pyrimidopyrimidine core structure.

BRIEF SUMMARY OF THE INVENTION

In a first aspect the present invention is directed to an efficient process for the manufacture of (E)-4-N,N-di-($C_{1-3}$)-alkylamino crotonic acid in HX salt form of formula I

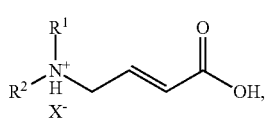

wherein $R^1$ and $R^2$ independently denote $C_{1-3}$-alkyl groups and $X^-$ denotes an acid anion, such as the chloride, bromide, tosylate, mesylate or trifluoroacetate anion, preferably chloride, with high quality, comprising the following synthesis steps:

a) step 1:

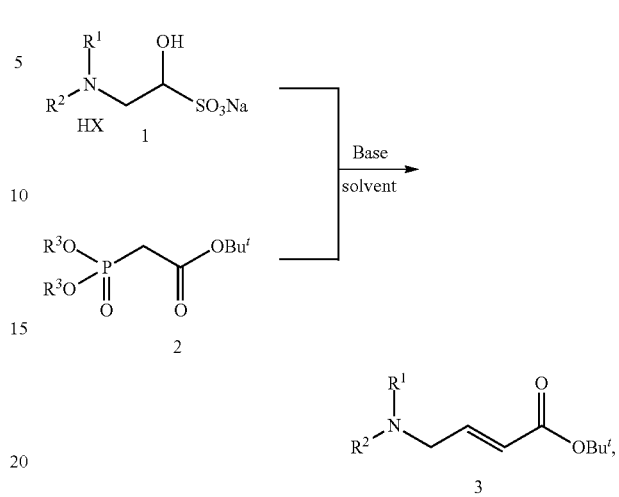

wherein $R^1$, $R^2$ and $R^3$ independently denote $C_{1-3}$-alkyl groups, OBu$^t$ denotes a tert-butyloxy group, HX denotes an acid selected from HCl, HBr, MeSO$_3$H, p-CH$_3$C$_6$H$_4$SO$_3$H (p-toluenesulfonic acid) and CF$_3$CO$_2$H, preferably HCl, the base preferably denotes a strong base such as alkali hydroxide, e.g. NaOH or KOH or the like, and solvent denotes water, a water miscible organic solvent such as MeOH or EtOH, and the mixtures thereof, preferably pure water or a mixture of water with MeOH or EtOH, b) step 2:

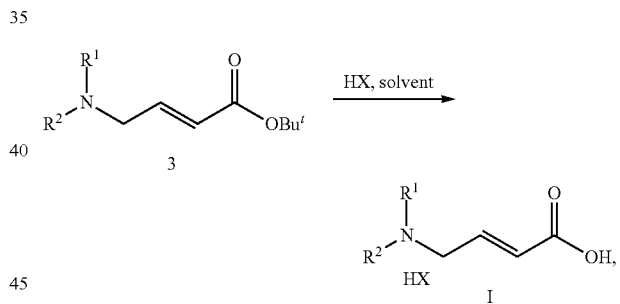

wherein $R^1$ and $R^2$ independently denote $C_{1-3}$-alkyl groups, OBu$^t$ denotes a tert-butyloxy group, HX denotes an acid, preferably an acid selected from HCl, HBr, MeSO$_3$H, p-CH$_3$C$_6$H$_4$SO$_3$H and CF$_3$CO$_2$H, most preferred the acid HCl, and solvent denotes a suitable solvent such as ethyl acetate, i-PrOAc, MTBE (methyl t-butyl ether), 2-MeTHF, MeCN, and dioxane, preferably ethyl acetate.

The second aspect of the invention is directed to the process for the manufacture of (E)-4-N,N-dialkylaminocrotonic acid in HCl salt form of formula I' using steps 1 and 2 described hereinbefore, wherein HX in both steps denotes HCl, and additional transformation of the hydrochloride salt of formula I' into the activated derivative (E)-4-N,N-dialkylamino-2-butenoylchloride hydrochloride II by c) step 3:

subsequent conversion of (E)-4-N,N-dialkylamino crotonic acid hydrochloride salt of compound I' into the activated derivative II

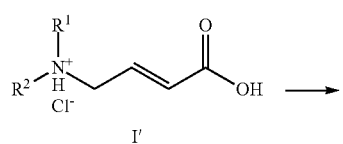

wherein $R^1$ and $R^2$ independently denote $C_{1-3}$-alkyl groups, with a chlorinating agent selected from thionylchloride, $POCl_3$, $PCl_3$ or $PCl_5$, preferably with thionylchloride.

Step 3 carried out by reaction of compound I with thionylchloride is of particular advantage since thionylchloride is significantly more stable than the other alternative reagents and provides improved operational safety in production scale. A second significant advantage of this variant is that reaction of compound II prepared with thionylchloride in step 4 described hereinafter leads to a very pure final product of formula III (more that 99%; HPLC) only applying simple purification steps.

In a third aspect the present invention is directed to a process for the manufacture of an EGFR tyrosine kinase inhibitor of general formula

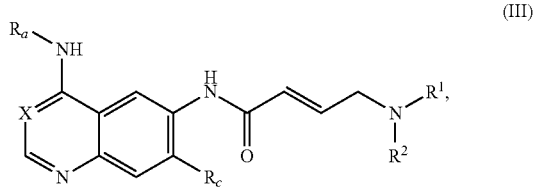

wherein X denotes a methine group substituted by a cyano group or a nitrogen atom, $R_a$ denotes a 3-chloro-4-fluorophenyl group, a 3-chloro-4-(pyridin-2-yl-methoxy)-phenyl group, or a 3-chloro-4-(3-fluoro-phenylmethoxy)-phenyl group, $R_c$ denotes a methoxy, ethoxy or tetrahydrofuran-3-yl-oxy group, and $R^1$ and $R^2$ independently denote $C_{1-3}$-alkyl groups, comprising the following synthesis steps 1 to 4:

a) step 1:

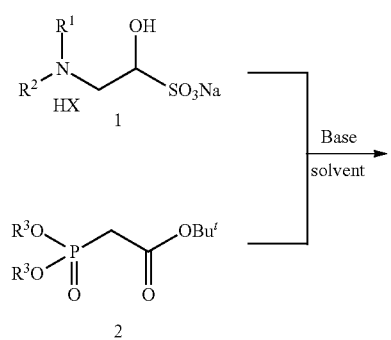

wherein $R^1$, $R^2$ and $R^3$ independently denote $C_{1-3}$-alkyl groups, $OBu^t$ denotes a tert-butyloxy group, and HX denotes an acid selected from HCl, HBr, $MeSO_3H$, $p-CH_3C_6H_4SO_3H$ and $CF_3CO_2H$, preferably the acid HCl, the base preferably denotes a strong base such as alkali hydroxide, e.g. NaOH, KOH or the like, and solvent denotes water, a water miscible organic solvent such as MeOH or EtOH, and the mixtures thereof, preferably pure water or a mixture of water with MeOH or EtOH, b) step 2:

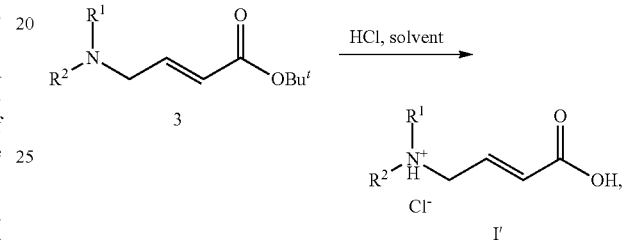

wherein $R^1$ and $R^2$ independently denote $C_{1-3}$-alkyl groups, $OBu^t$ denotes a tert-butyloxy group, and solvent denotes a suitable solvent such as ethyl acetate, i-PrOAc, MTBE (methyl t-butyl ether), 2-MeTHF, MeCN, and dioxane, preferably ethyl acetate, c) step 3:

subsequent conversion of (E)-4-N,N-di-($C_{1-3}$)-alkylamino crotonic acid hydrochloride salt of compound I' into the activated derivative II

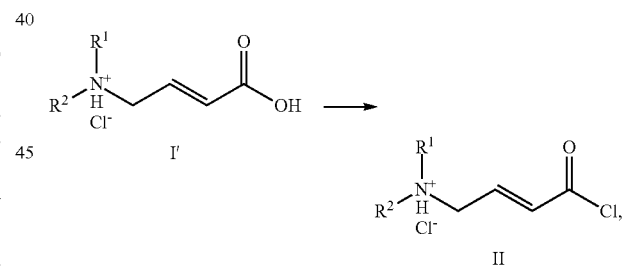

wherein $R^1$ and $R^2$ independently denote $C_{1-3}$-alkyl groups, with a chlorinating agent selected from thionylchloride, $POCl_3$, $PCl_3$ or $PCl_5$, preferably with thionylchloride, and e) step 4:

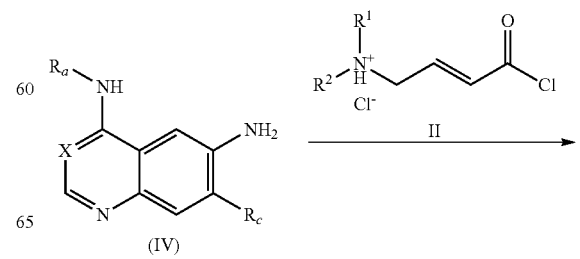

-continued

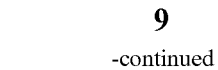
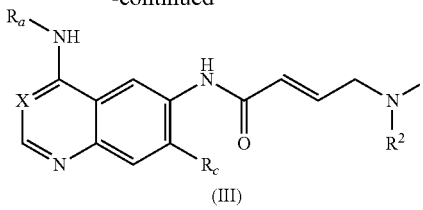

(III)

wherein X denotes a methine group substituted by a cyano group or a nitrogen atom,
$R_a$ denotes a 3-chloro-4-fluorophenyl group, a 3-chloro-4-(pyridin-2-yl-methoxy)-phenyl group, or a 3-chloro-4-(3-fluoro-phenylmethoxy)-phenyl group,
$R_c$ denotes a methoxy, ethoxy or tetrahydrofuran-3-yl-oxy group, and
$R^1$ and $R^2$ independently denote $C_{1-3}$-alkyl groups.

DETAILED DESCRIPTION OF THE INVENTION

In a first aspect this invention describes an efficient process for the manufacture of (E)-4-N,N-di-($C_{1-3}$)-alkylamino crotonic acid in HX acid addition salt form, such as the hydrochloride, hydrobromide, the methanesulfonate salt, p-toluolsulfonate salt and trifluoroacetate, preferably the hydrochloride, and as an activated derivative (E)-4-N,N-di-($C_{1-3}$)-alkylamino-2-butenoylchloride hydrochloride, using commercially available starting material in a convergent manner, providing the desired product with very high quality. Key step 1 takes advantage of a highly stereoselective olefination reaction so that a convergent synthetic strategy could be implemented and consequently secures high efficiency. Thus compound I wherein $R^1$ and $R^2$ independently denote $C_{1-3}$-alkyl groups) could be obtained through 3 linear steps in overall more than 71% yield, starting from commercially available educts (Scheme 5):

I wherein $R^1$ and $R^2$ independently denote methyl or ethyl groups, preferably methyl groups, and $X^-$ denotes an acid anion, such as the chloride, bromide, tosylate, mesylate or trifluoroacetate anion, preferably the chloride anion, with high quality, comprising the following synthesis steps:

a) step 1:

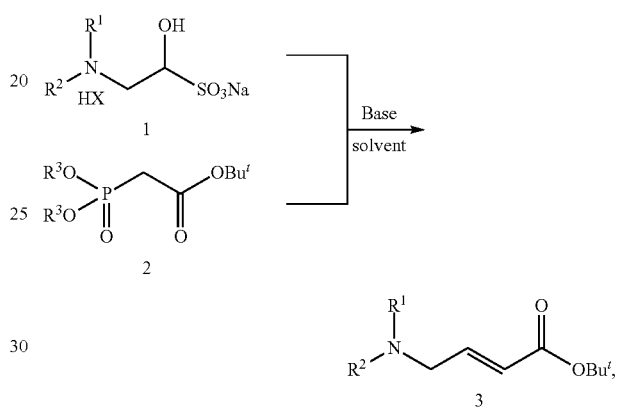

wherein $R^1$ and $R^2$ independently denote methyl or ethyl groups, preferably methyl groups, $R^3$ independently denote $C_{1-3}$-alkyl groups, $OBu^t$ denotes a tert-butyloxy group, HX Scheme 5 An efficient process to compound I.

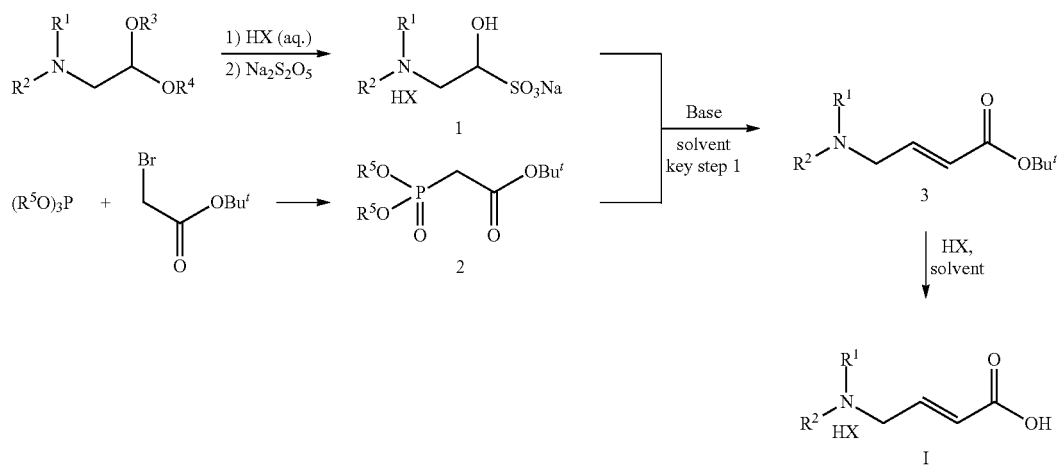

Preferred Embodiments of the First Aspect of the Invention

In a preferred embodiment the first aspect of the invention is directed to an efficient process for the manufacture of (E)-4-N,N-di-($C_{1-3}$)-alkylamino crotonic acid in HX salt form of formula I denotes an acid selected from HCl, HBr, $MeSO_3H$, p-$CH_3C_6H_4SO_3H$ (p-toluenesulfonic acid) and $CF_3CO_2H$, preferably HCl, the base preferably denotes an alkali hydroxide selected from NaOH and KOH, preferably NaOH, and solvent denotes water, a water miscible organic solvent such as MeOH or EtOH, and the mixtures thereof, preferably pure water or a mixture of water with MeOH or EtOH, b) step 2:

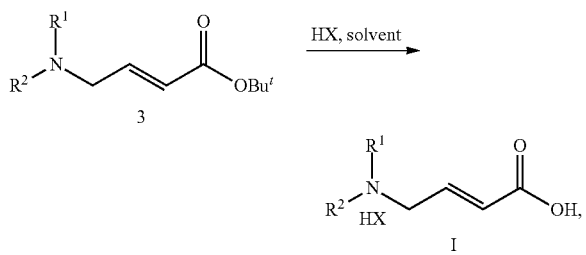

wherein $R^1$ and $R^2$ independently denote methyl or ethyl groups, preferably methyl groups, OBu$^t$ denotes a tert-butyloxy group, HX denotes an acid selected from HCl, HBr, MeSO$_3$H, p-CH$_3$C$_6$H$_4$SO$_3$H and CF$_3$CO$_2$H, preferably HCl, and solvent denotes a suitable solvent such as ethyl acetate, i-PrOAc, MTBE (methyl t-butyl ether), 2-MeTHF, MeCN, and dioxane, preferably ethyl acetate.

Preferred Embodiments of the Second Aspect of the Invention

In a preferred embodiment the second aspect of the invention is directed to the process for the manufacture of (E)-4-N,N-dialkylaminocrotonic acid in HCl salt form of formula I' using steps 1 and 2 described under the preferred embodiment of the first aspect of the invention and additional transformation of the hydrochloride salt of formula I' into the activated derivative (E)-4-N,N-di-(C$_{1-3}$)-alkylamino-2-butenoylchloride hydrochloride II by
c) step 3:
subsequent conversion of (E)-4-N,N-dialkylamino crotonic acid hydrochloride salt of compound I' into the activated derivative II

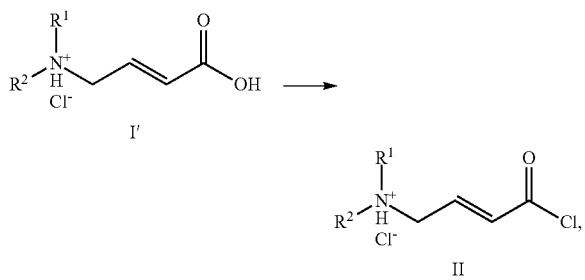

wherein $R^1$ and $R^2$ independently denote methyl or ethyl groups, preferably methyl groups, with thionylchloride as the chlorinating agent.

The reaction of step 3 may be carried out by dropwise addition of thionylchloride at 10 to −10° C., preferably at 0 to −5° C., into a solution of (E)-4-N,N-dialkylamino crotonic acid hydrochloride in a polar aprotic solvent such as N-methylpyrrolidone (NMP), acetone, N,N-Dimethylformamide (DMF), Acetonitrile or dimethyl sulfoxide (DMSO), preferably NMP.

Preferred Embodiments of the Third Aspect of the Invention

In a preferred embodiment the third aspect of the invention is directed to a process for the manufacture of an EGFR tyrosine kinase inhibitor of general formula

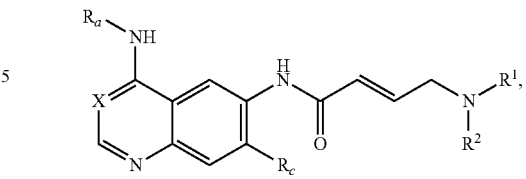

wherein X denotes a nitrogen atom,
$R_a$ denotes a 3-chloro-4-fluorophenyl group,
$R_c$ denotes a tetrahydrofuran-3-yl-oxy group, and
$R^1$ and $R^2$ both denote methyl groups,
comprising the following synthesis steps:
a) step 1:

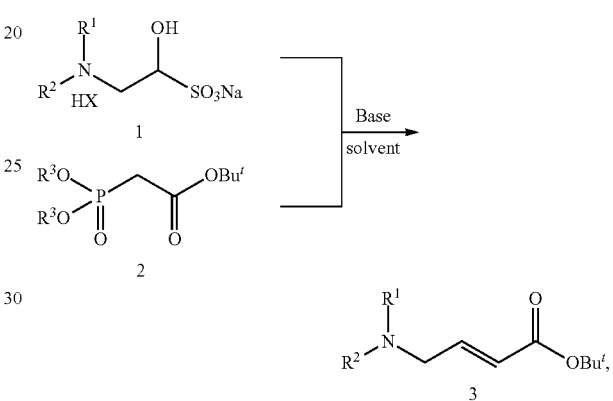

wherein $R^1$ and $R^2$ both denote methyl groups, $R^3$ independently denote C$_{1-3}$-alkyl groups, OBu$^t$ denotes a tert-butyloxy group, HX denotes an acid selected from HCl, HBr, MeSO$_3$H, p-CH$_3$C$_6$H$_4$SO$_3$H (p-toluenesulfonic acid) and CF$_3$CO$_2$H, preferably HCl, the base preferably denotes an alkali hydroxide selected from NaOH and KOH, preferably NaOH, and solvent denotes water, a water miscible organic solvent such as MeOH or EtOH, and the mixtures thereof, preferably pure water or a mixture of water with MeOH or EtOH,
b) step 2:

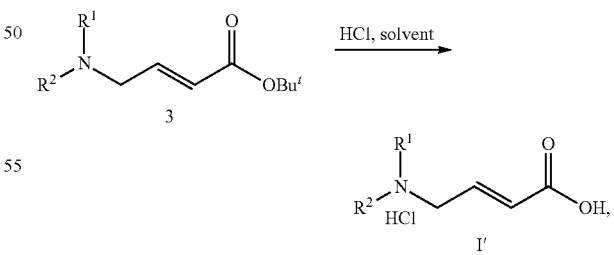

wherein $R^1$ and $R^2$ both denote methyl groups, OBu$^t$ denotes a tert-butyloxy group, and solvent denotes a suitable solvent such as ethyl acetate, i-PrOAc, MTBE (methyl t-butyl ether), 2-MeTHF, MeCN, and dioxane, preferably ethyl acetate,
c) step 3:
subsequent conversion of (E)-4-N,N-dimethylamino crotonic acid hydrochloride salt I' into the activated derivative II

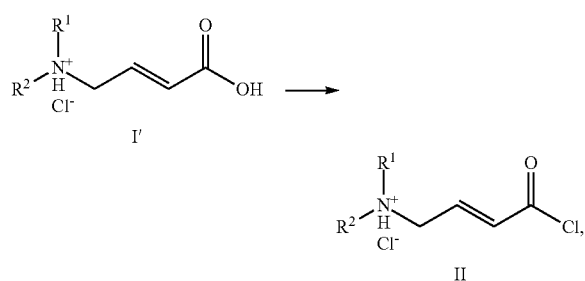

I' wherein R¹ and R² both denote methyl groups, with thionyl-chloride as the chlorinating agent, and e) step 4:

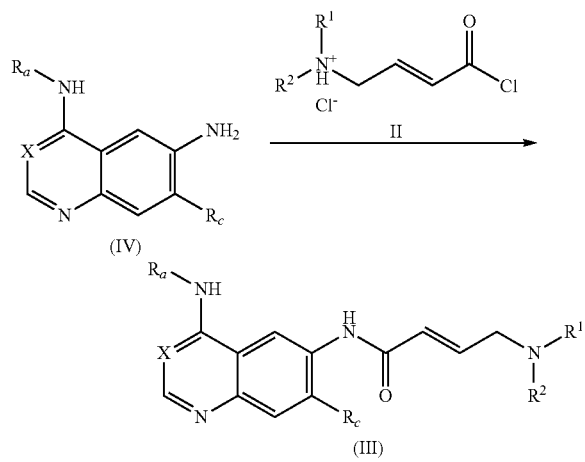

wherein X denotes a nitrogen atom,
$R_a$ denotes the 3-chloro-4-fluorophenyl group,
$R_c$ denotes a tetrahydrofuran-3-yl-oxy group, and
R¹ and R² both denote methyl groups.

The reaction of step 3 may be carried out by dropwise addition of thionylchloride at 10 to −10° C., preferably at 0 to −5° C., into a solution of (E)-4-N,N-dialkylamino crotonic acid hydrochloride in a polar aprotic solvent such as N-methylpyrrolidone (NMP), acetone, N,N-Dimethylformamide (DMF), Acetonitrile or dimethyl sulfoxide (DMSO), preferably NMP, The amid formation of step 4 may be carried out by dropwise addition of the (E)-4-N,N-dialkylamino crotonic acid chloride solution prepared according to step 3 into a solution of the compound of formula IV in a polar aprotic solvent such as N-methylpyrrolidone (NMP), acetone, N,N-Dimethylformamide (DMF), Acetonitrile or dimethyl sulfoxide (DMSO), preferably NMP at 10 to −10° C., preferably at 0 to −5° C.

This invention describes an efficient process for preparation of (E)-4-N,N-dialkylamino crotonic acid addition salts such as preferably the hydrochloride, which is a suitable starting compound for the preparation of activated derivatives such as (E)-4-N,N-dialkylamino crotonic acid chloride, suitable as a valuable intermediates in the synthesis of EGFR tyrosine kinase inhibitors based on a quinazoline, quinoline or pyrimidopyrimidine core structure. Specific reaction conditions and advantages of the process according to the invention are (1) Key step 1 uses a highly stereoselective olefination reaction designed to assemble the target compound, which employs dialkylamino group functionalized starting material directly and thus avoids the possibility of the formation of 3,4-bis(dialkylamino)butanoic acid derivatives byproduct as reported in WO 2010/131921.

(2) Preferred solvent for step 1 is water, MeOH, EtOH, or a mixture thereof, the preferred solvent is Water. Step 1 can be performed preferably by adding aqueous base solution into the mixture of compounds 1 and 2 in water or, in the alternative, by adding aqueous solution of compound 1 into the mixture of compound 2 and base in water. The base employed in Step 1 may be, for example, NaOH, KOH, and LiOH, NaOH is preferred in this invention considering the lower costs. Temperature range for Step 1 is −10° C. to 30° C., preferably 0° C. to 20° C. Molar ratio of NaOH to 1 to 2 is in the range of about 3.5-10 to 1.05-1.5 to 1.0, preferably 3.5-4.0 to 1.05-1.2 to 1.0.

(3) Compound 3 with a t-butyl ester moiety is a key intermediate, which is stable under basic condition employed in Step 1 without the formation of potential byproduct 4-dialkylamino-3-hydroxybutanoic acid or derivatives thereof observed according to WO 2004/066919 and WO 2010/131921. Advantageously, compound 3 can be easily isolated by simple extraction with an organic solvent, and can be used directly in the next reaction step without further purification. Suitable organic solvents include but are not limited to MTBE (methyl t-butyl ether), 2-MeTHF, and i-PrOAc.

(4) The mild reaction condition and using organic solvent for the hydrolysis of compound 3 (Step 2) could effectively suppress the formation byproducts and simplify the work-up. The hydrolysis is performed at a temperature from −10° C. to 30° C., preferably at 5° C. to 25° C. Organic solvents could be EtOAc, MTBE, 2-MeTHF, MeCN, and dioxane, preferably EtOAc. And 2.5-10 equiv. of hydrochloric acid in organic solvent with concentration ranging from 1.0-8.0 mol/L is used.

(5) Following the synthetic route developed in this invention, last purification of the (E)-4-N,N-dialkylamino crotonic acid in HX salt form of formula I could be easily realized by simple operation like re-slurry instead of recrystallization. And it was found that a recrystallization in i-PrOH as documented in WO 2010/131921 could lead to the formation of corresponding i-propyl ester (up to 3.5 area-%, HPLC) when performed on large scale. Suitable solvents to perform re-slurry include MeCN, acetone, and MIBK, preferably MeCN.

(6) The preparation of the (E)-4-N,N-dialkylamino-2-butenoylchloride hydrochloride II of in step 3, especially of the dimethylamino crotonic acid chloride, is advantageously carried out using thionylcloride as the chlorinating agent, added dropwise with cooling at preferably at 0 to −5° C., into a solution of (E)-4-N,N-dialkylamino crotonic acid hydrochloride in a polar aprotic solvent such as N-methylpyrrolidone (NMP), acetone, N,N-Dimethylformamide (DMF), Acetonitrile or dimethyl sulfoxide (DMSO), preferably NMP. Thionylchloride is by far preferred in this step compared to other chlorinating agents which may be considered suitable for this purpose such as oxalic acid chloride, oxalic acid ethylester chloride, POCl₃, PCl₃ or PCl₅, regarding operational safety. Furthermore, the chlorinated product can be directly used in the amid formation step 4 without intermediate purification step and allows to obtain a very pure final product of formula III (more that 99%; HPLC) only applying simple purification steps.

(7) In its most preferred embodiment the amid formation of step 4 is carried out by dropwise addition of (E)-4-N,N-dialkylamino-2-butenoylchloride hydrochloride II solution in a polar aprotic solvent such as N-methylpyrrolidone (NMP), N,N-Dimethylformamide (DMF) or Acetonitrile, preferably NMP, prepared according to step 3, into a solution of 6-amino-4-[(3-chloro-4-fluorophenyl)amino]-7-((S)-tetrahydrofuran-3-yloxy)-quinazoline in the same a polar aprotic solvent at 10 to −10° C., preferably at 0 to −5° C. Purification is carried out by addition of water, adjusting pH >9 and extraction with an ester such as ethyl acetate or, preferably, butyl acetate. The polar aprotic solvent is removed by extraction with water and the remaining organic phase is concentrated by evaporation. After addition of small amounts of water and methylcyclohexane crystallization of the product may be induced by inoculation.

The following Examples are intended to illustrate the invention in more detail:

Example 1

Preparation of Compound 1 ($R^1$=$R^2$=Me)

Sodium 2-Dimethylamino-1-hydroxy-ethanesulfonate

To a 5 L jacket reactor, (Dimethylamino)acetaldehyde diethyl acetal (400 g) and Water (200 mL) is charged at room temperature. Start agitation and cool the system down to 0° C., then Conc. HCl aqueous solution (37 wt %, 480 g) is added within 1 h, followed by stirring at 40° C. for 4 h. At this point, a solution of sodium metasulphite (424 g) in water (720 mL) is added into the above system within 40 min, and keep stirring at 40° C. for 2 h. The ethanol (2 L) is added and cool the mixture to 0° C., followed by filteration and washing with ethanol to get a white cake, which is dried in vacuo at 45° C. for 6 h to give desired compound 1 in 84% yield (474 g) and >98% NMR purity.

Example 2

Preparation of Compound 2 ($R^3$=Et)

(Diethoxy-phosphoryl)-acetic acid tert-butyl ester

Triethyl phosphite (485 g) is warmed up to 90° C. under $N_2$ atmosphere in a three-necked round-bottomed flask, and t-butyl bromoacetate (541 g) is added dropwise into the system within 2 h. Then the mixture is kept stirring at 90° C. for around 4 h, and then cooled to room temperature. The obtained mixture is distilled under vacuo to remove compounds with low boiling point, and the residue is collected as a colorless liquid compound 5 in 97% yield (680 g) and >98% GC purity.

Example 3

Preparation of Compound 3 ($R^1$=$R^2$=Me)

(E)-4-Dimethylamino-but-2-enoic acid tert-butyl ester

Charge tert-Butyl diethyl phosphonoacetate (3, 252 g), sulphite adduct (2, 240 g) and water (720 mL) to a 5 L jacket reactor, and cool the mixture down to 0° C. A solution of NaOH aqueous solution (2.5 mol/L, 1.5 L) is added dropwise into the system within 1 h, and keep stirring at this temperature until process monitoring indicates less than 5 area % compound 3 remains. The mixture is extracted with MTBE (1 L×3), followed by distillation under vacuo to give compound 3 as a pale-yellow liquid in 100% yield (185 g) and 92% GC purity, which is used directly for the next step without further purification.

Example 4

Preparation of Compound I ($R^1$=$R^2$=Me)

(E)-4-Dimethylamino-crotonic acid hydrochloride

Synthesis Step:
Crude compound 3 (105 g) and EtOAc (80 mL) are charged to a 2 L jacket reactor and cool down to 10° C. under $N_2$ atmosphere. To this system, hydrochloric acid solution in EtOAc (5 mol/L, 750 mL) is added dropwise at temperature in the range of 10~25° C., and keep stirring at 20~25° C. until process monitoring indicates less than 1 area % compound 3 remains. Cool the system down to 0° C. and perform filtration, washing with EtOAc (1 L) to get a wet cake, which is dried under vacuo at 45° C. to deliver (E)-4-N,N-dimethylamino crotonic acid hydrochloride as a white solid in 92% yield (79 g) and 97.5% HPLC purity.

Purification Step:
The (E)-4-N,N-dimethylamino crotonic acid hydrochloride obtained above (60 g) and MeCN (480 mL) are charged to a 750 mL jacket reactor. Heat the mixture up to 85° C. and keep stirring at this temperature for 1.5 h. Perform filtration after cooling the system down to room temperature, the white cake is then dried under vacuo to deliver (E)-4-N,N-dimethylamino crotonic acid hydrochloride as a white solid in 93% yield (56 g) and 99.5% HPLC purity.

Example 5

Preparation of Compound II ($R^1$=$R^2$=Me)

(E)-4-N,N-dialkylamino-2-butenoylchloride hydrochloride

Synthesis Step:
9.66 g of (E)-4-Dimethylamino-crotonic acid hydrochloride (0.055 Mol) in 90 ml of NMP are cooled down to 0 to −5° C. 6.6 g (0.055 Mol) of thionyl chloride are added dropwise into this solution within 5 to 10 minutes, thereafter purging with 3 ml of NMP. The reaction mixture is kept stirring for about 20 minutes at 0 to −5° C.

Purification Step:
The product solution can be used without further purification.

Example 6

Preparation of Compound III (X=N, $R_a$=3-chloro-4-fluorophenyl, $R_c$=tetrahydrofuran-3-yl-oxy, $R^1$=$R^2$=Me)

4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline Synthesis Step:
12.46 g of 6-amino-4-[(3-chloro-4-fluorophenyl)amino]-7-((S)-tetrahydrofuran-3-yloxy)-quinazoline (0.033 Mol) with a water content of at max 0.15% in 60 ml of NMP are added dropwise within 15 to 30 minutes at 0 to −5° C. into the product solution prepared according to Example 5. The reaction mixture is kept stirring for about 15 minutes. Reaction control by HPLC shows a content <1% of the educt amine.

Purification Step:

100 ml of water are added dropwise under control of heat evolution at 15° C. max. About 23 g 50% NaOH solution are added at 25° C. at max to adjust to pH >9. The alcaline water phase is extracted 3 times by stirring with 400 ml of butyl acetate. Afterwards the organic phase is extracted 3 times by stirring with 100 ml of water in order to remove NMP. The organic phase is evaporated at 60° C. max and 100-300 mbar and concentrated to a volume of about 80 ml, then 12.2 ml of methylcyclohexane and 2 ml of water are added and crystallization of the product is induced by inoculation, slowly cooling down to ambient temperature. The product is filtered with suction, washed with 60 ml of methylcyclohexane and dried at reduced pressure at 40° C.

Yield: 14.1 g (87%), purity: 99.64% (HPLC).

The invention claimed is:

1. A process for the manufacture of (E)-4-N,N-di-(C$_{1-3}$)-alkylamino crotonic acid in HX salt form of formula I

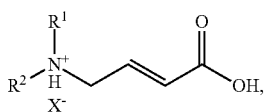

wherein R$^1$ and R$^2$ independently denote C$_{1-3}$-alkyl groups and X$^-$ denotes an acid anion, comprising the following synthesis steps:

a) step 1:

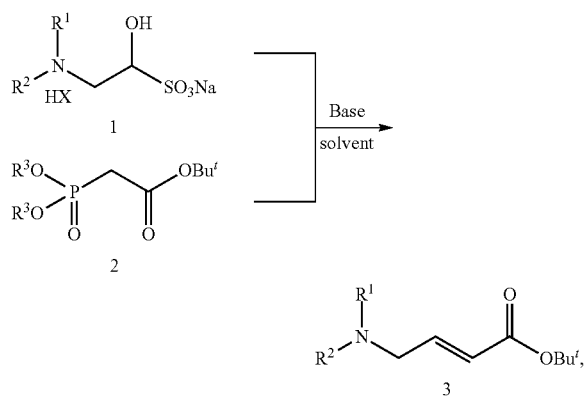

wherein R$^1$, R$^2$ and R$^3$ independently denote C$_{1-3}$-alkyl groups, OBu$^t$ denotes a tert-butyloxy group, HX denotes an acid selected from HCl, HBr, MeSO$_3$H, p-CH$_3$C$_6$H$_4$SO$_3$H (p-toluenesulfonic acid) and CF$_3$CO$_2$H, the base denotes a strong base, and solvent denotes water, a water miscible organic solvent, and the mixtures thereof, and b) step 2:

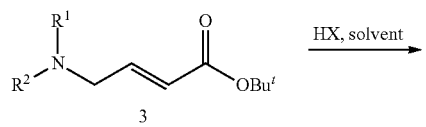

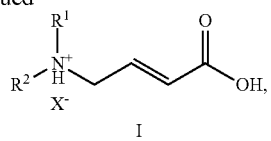

wherein R$^1$ and R$^2$ independently denote C$_{1-3}$-alkyl groups, OBu$^t$ denotes a tert-butyloxy group, HX denotes an acid, and solvent denotes a suitable solvent.

2. The process of claim 1 for the manufacture of (E)-4-N,N-dimethylamino crotonic acid in HX salt form wherein R$^1$ and R$^2$ denote methyl groups, R$^3$ independently denote C$_{1-3}$-alkyl groups, in step 1 HX denotes HCl, the base denotes NaOH, and the solvent denotes pure water or a mixture of water with MeOH or EtOH, and in step 2 HX denotes HCl and the solvent denotes ethyl acetate.

3. The process of claim 1, wherein HX in both steps denotes HCl, and further comprising converting (E)-4-N,N-di-(C$_{1-3}$)-alkylamino crotonic acid hydrochloride salt of compound I' according to c) step 3:

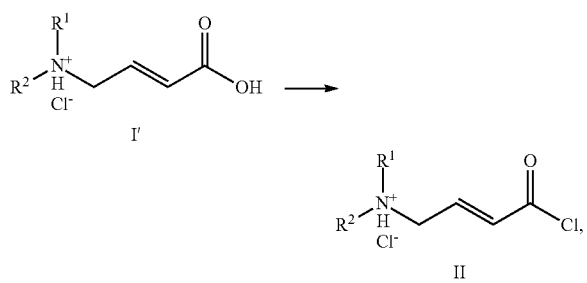

wherein R$^1$ and R$^2$ independently denote C$_{1-3}$-alkyl groups, with a chlorinating agent selected from thionylchloride, POCl$_3$, PCl.

4. The process according to claim 3, wherein R$^1$ and R$^2$ denote methyl groups, and the chlorinating agent is thionyl chloride.

5. A process for the manufacture of formula (III)

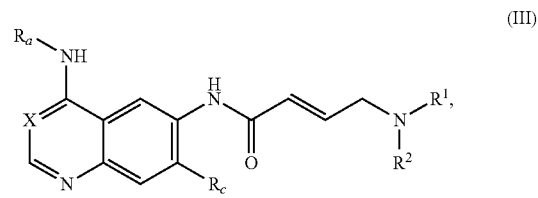

wherein X denotes a methine group substituted by a cyano group or a nitrogen atom, R$_a$ denotes a 3-chloro-4-fluorophenyl group, a 3-chloro-4-(pyridin-2-yl-methoxy)-phenyl group, or a 3-chloro-4-(3-fluoro-phenylmethoxy)-phenyl group, R$_c$ denotes a methoxy, ethoxy or tetrahydrofuran-3-yl-oxy group, and R$^1$ and R$^2$ independently denote C$_{1-3}$-alkyl groups, comprising:

a) step 1:

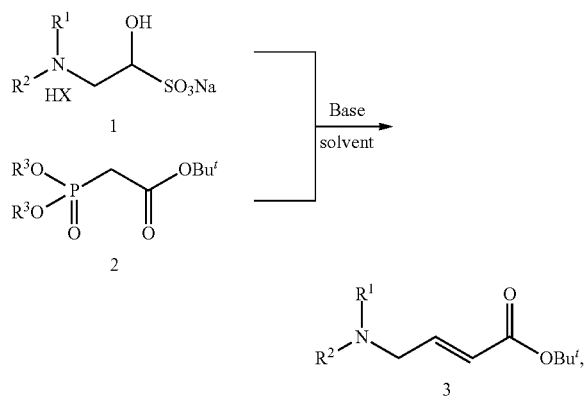

wherein $R^1$, $R^2$ and $R^3$ independently denote $C_{1-3}$-alkyl groups, $OBu^t$ denotes a tert-butyloxy group, and HX denotes an acid selected from HCl, HBr, $MeSO_3H$, $p\text{-}CH_3C_6H_4SO_3H$ and $CF_3CO_2H$, the base denotes a strong base, and solvent denotes water, a water miscible organic solvent, and the mixtures thereof, b) step 2:

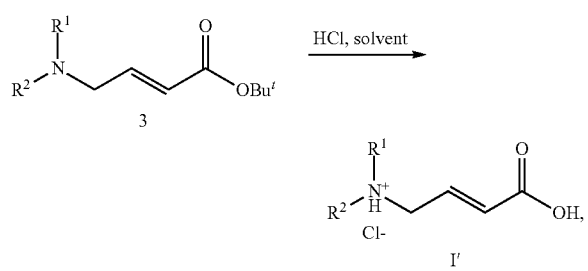

wherein $R^1$ and $R^2$ independently denote $C_{1-3}$-alkyl groups, $OBu^t$ denotes a tert-butyloxy group, and solvent denotes selected from ethyl acetate, i-PrOAc, MTBE (methyl t-butyl ether), 2-MeTHF, MeCN, and dioxane, c) step 3:

subsequent conversion of (E)-4-N,N-dialkylamino crotonic acid hydrochloride salt of compound I' into the activated derivative II

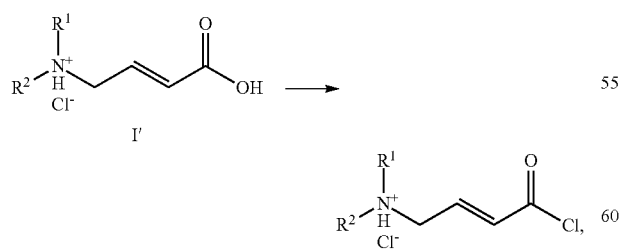

wherein $R^1$ and $R^2$ independently denote $C_{1-3}$-alkyl groups, with a chlorinating agent selected from thionyl-chloride, $POCl_3$, $PCl_5$, and e) step 4:

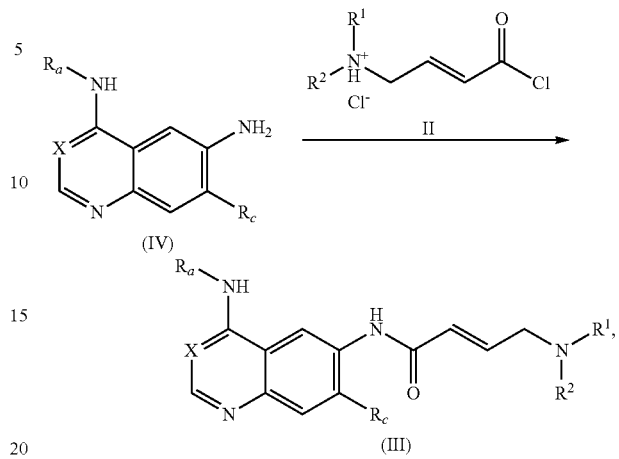

wherein X denotes a methine group substituted by a cyano group or a nitrogen atom, $R_a$ denotes a 3-chloro-4-fluorophenyl group, a 3-chloro-4-(pyridin-2-yl-methoxy)-phenyl group, or a 3-chloro-4-(3-fluoro-phenylmethoxy)-phenyl group, $R_c$ denotes a methoxy, ethoxy or tetrahydrofuran-3-yl-oxy group, and $R^1$ and $R^2$ independently denote $C_{1-3}$-alkyl groups.

6. The process of claim 5, wherein wherein X denotes a nitrogen atom, $R_a$ denotes a 3-chloro-4-fluorophenyl group, $R_c$ denotes a tetrahydrofuran-3-yl-oxy group, and $R^1$ and $R^2$ both denote methyl groups, comprising the following synthesis steps:

a) step 1:

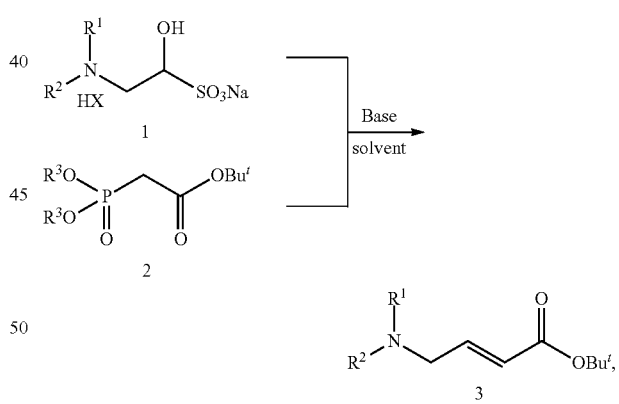

wherein $R^1$ and $R^2$ both denote methyl groups, $R^3$ independently denote $C_{1-3}$-alkyl groups, $OBu^t$ denotes a tert-butyloxy group, HX denotes HCl, the base denotes an alkali hydroxide, and solvent denotes water, a water miscible organic solvent, b) step 2:

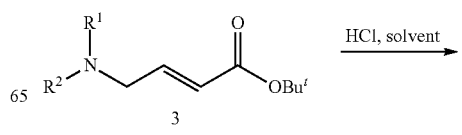

-continued

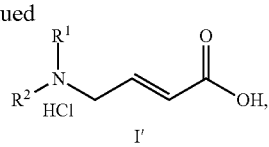
I' wherein $R^1$ and $R^2$ both denote methyl groups, OBu$^t$ denotes a tert-butyloxy group, and solvent denotes a solvent selected from such as ethyl acetate, i-PrOAc, MTBE (methyl t-butyl ether), 2-MeTHF, MeCN, and dioxane, c) step 3:

subsequent conversion of (E)-4-N,N-dimethylamino crotonic acid hydrochloride salt I' into the activated derivative II

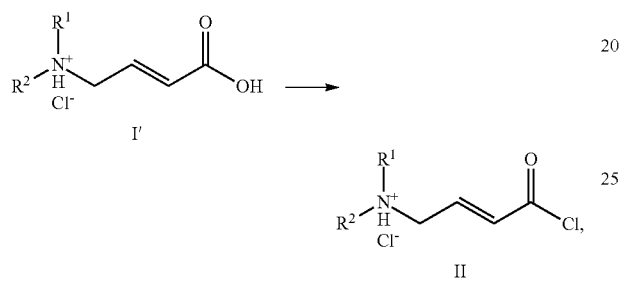

wherein $R^1$ and $R^2$ both denote methyl groups, with thionylchloride as the chlorinating agent,
and e) step 4:

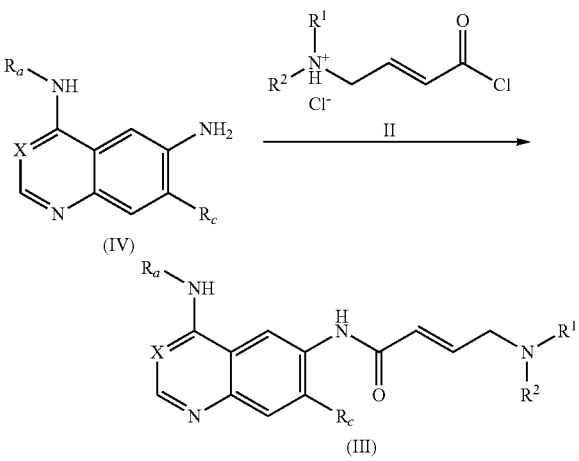

wherein X denotes a nitrogen atom,
$R_a$ denotes the 3-chloro-4-fluorophenyl group,
$R_c$ denotes a tetrahydrofuran-3-yl-oxy group, and $R^1$ and $R^2$ both denote methyl groups.

* * * * *